US009267866B2

(12) United States Patent
Almirall et al.

(10) Patent No.: US 9,267,866 B2
(45) Date of Patent: Feb. 23, 2016

(54) CAPILLARY MICROEXTRACTOR OF VOLATILES (CMV)

(71) Applicants: Jose Almirall, Miami, FL (US); Wen Fan, Miami, FL (US)

(72) Inventors: Jose Almirall, Miami, FL (US); Wen Fan, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 57 days.

(21) Appl. No.: 14/206,250

(22) Filed: Mar. 12, 2014

(65) Prior Publication Data

US 2014/0260974 A1    Sep. 18, 2014

Related U.S. Application Data

(60) Provisional application No. 61/779,690, filed on Mar. 13, 2013.

(51) Int. Cl.
| | |
|---|---|
| *G01N 1/22* | (2006.01) |
| *G01N 1/20* | (2006.01) |
| G01N 30/08 | (2006.01) |
| G01N 1/02 | (2006.01) |
| G01N 30/60 | (2006.01) |

(Continued)

(52) U.S. Cl.
CPC ............ *G01N 1/2214* (2013.01); *G01N 1/2035* (2013.01); *G01N 30/08* (2013.01); *G01N 30/6095* (2013.01); *G01N 30/72* (2013.01); *G01N 2001/022* (2013.01); *G01N 2001/2223* (2013.01); *G01N 2030/009* (2013.01); *G01N 2030/062* (2013.01); *G01N 2030/085* (2013.01); *G01N 2030/143* (2013.01)

(58) Field of Classification Search
CPC ....... G01N 1/2214; G01N 1/40; G01N 1/405; G01N 2001/022; G01N 30/08; G01N 2030/085; G01N 2030/143
See application file for complete search history.

(56) References Cited

U.S. PATENT DOCUMENTS

| | | | |
|---|---|---|---|
| 2002/0150923 A1* | 10/2002 | Malik | ............................... 435/6 |
| 2009/0084201 A1 | 4/2009 | Almirall et al. | |
| 2009/0309016 A1* | 12/2009 | Almirall et al. | ............... 250/282 |

OTHER PUBLICATIONS

Guerra, P. et al., "Analysis of the volatile chemical markers of explosives using novel solid phase microextraction coupled to ion mobility spectrometry," *J. Sep. Sci.*, 2008, pp. 2891-2898, vol. 31.

(Continued)

*Primary Examiner* — Robert Clemente
(74) *Attorney, Agent, or Firm* — Saliwanchik, Lloyd & Eisenschenk

(57) ABSTRACT

A capillary microextractor of volatiles (CMV) allows the sampling of diagnostic volatiles that can be an explosive, explosive taggant, drug, poison, decomposition products thereof, a mixture of chemicals comprising an odor signature determined from detector dog trials, or volatile organic compounds indicative of a disease or other medical condition. The CMV has a thermally stable housing with orifices to allow the contact of a gas that contains one or more diagnostic volatiles with an absorbent that extracts and concentrates the diagnostic volatiles. After sampling, the CMV with the absorbed diagnostic volatiles can be placed in an ionized gas beam and introduced into a mass spectrometer or placed in a thermal desorption unit (TDU), where, upon heating, the diagnostic volatiles are released to an inlet port of an analytical instrument. Analytical instruments that can be used include gas chromatographs and ion mobility spectrometers for separation and mass spectrometers for unambiguous identification of the diagnostic volatiles.

13 Claims, 4 Drawing Sheets

(51) Int. Cl.
G01N 30/72 (2006.01)
G01N 30/14 (2006.01)
G01N 30/00 (2006.01)
G01N 30/06 (2006.01)

(56) References Cited

OTHER PUBLICATIONS

Guerra-Diaz, P. et al., "Dynamic Planar Solid Phase Microextraction-Ion Mobility Spectrometry for Rapid Field Air Sampling and Analysis of Illicit Drugs and Explosives," *Anal. Chem.*, 2010, pp. 2826-2835, vol. 82.

Lai, H. et al., "Identification of volatile chemical signatures from plastic explosives by SPME-GC/MS and detection by ion mobility spectrometry," *Anal Bioanal Chem*, 2010, pp. 2997-3007, vol. 396.

Liu, W. et al., "Physically incorporated extraction phase of solid-phase microextraction by sol-gel technology," *Journal of Chromatography A*, 2006, pp. 37-43, vol. 1102.

* cited by examiner

US 9,267,866 B2

CAPILLARY MICROEXTRACTOR OF VOLATILES (CMV)

CROSS-REFERENCE TO RELATED APPLICATION

The present application claims the benefit of U.S. Provisional Application Ser. No. 61/779,690, filed Mar. 13, 2013, which is hereby incorporated by reference herein in its entirety, including any figures, tables, or drawings.

BACKGROUND OF INVENTION

Providing for the general safety of the population and enforcing the laws to this effect have become more challenging. Rapid and accurate sampling and detection of explosives, illicit drugs, and dangerous chemicals within the environment, particularly at points of entry, such as, ports and airports, and at populated facilities, such as, public transportation, sporting arenas, and recreational facilities, is increasingly required. This analysis requires a method that can identify specific chemicals, particularly organic molecules, and unknown chemical that is not only accurate and specific, but increasingly in a manner that is rapid and can be carried out with extremely small sample sizes. For example, nearly 90% of the world's cargo is moved by sea, yet nearly 98% of the containers are not inspected because the screening methodology is lacking to identify the potential threats in an effective manner. A screening technique for these chemical dangers must be very rapid, sensitive, and easily carried out with minimal modification of the infrastructure.

Methods that have been employed for analysis are generally those that separate and detect volatile compounds, such as those using gas chromatography coupled to a mass spectrometer (GC-MS) or ion mobility spectrometry (IMS), in a variety of modes in which they can be configured to carry out reasonably rapid analysis. Particularly desirable are portable devices that can be shared between multiple sites. Additionally, simple sampling devices that can rapidly sample a gas and collect a sufficient amount of analyte are necessary to achieve a reasonable level of assurance that threats have been assessed sufficiently and fairly.

For example, the Transportation Security Administration (TSA) has mandated that every airport in the United States screen all bags for explosives. IMS is an approved screening tool, because it can detect many organic compounds in an accurate, extremely fast, and straightforward manner that is extremely sensitive while being low in cost to perform. Analysis using commercial IMS devices can be carried out in one to seven seconds. There are more than 60,000 IMS units situated throughout the world, which means that virtually all populated areas probably have an IMS device sufficiently close to a suspected site to deliver a sample rapidly to the machine.

Sampling of the air is often carried out using a solid phase microextraction (SPME) device, which provides a large surface area to absorb a target chemical rapidly with a sufficient extraction capacity and efficiency. Variations on this technology continue to be explored with the goal of enabling sampling and analysis during a sufficiently small window of time to achieve a level of comfort that the threat is discovered before that threat becomes an event.

Such sampling devices and methodology can be used for threats that are of smaller scope, but where high rapidity and accuracy is desirable. For example, detection of drugs or indicators of drugs are needed for determination that recreational drugs are not impairing an automobile driver or a technician carrying out a potentially dangerous task in construction or manufacturing. Additionally, similar sampling devices and methodology could be used for the diagnosis of diseases or assessment of an individual's health. To this end, a rapid and effective volatiles sampling device that can be readily adapted to IMS, GC-MS, or other equipment and can be employed any site and, as needed, readily transported to an analysis facility is desired.

BRIEF SUMMARY

Embodiments of the invention are directed to a device for sampling an air, or other gas, sample and the use of the device for sampling and analyzing for diagnostic volatiles. The diagnostic volatiles are those that indicate a targeted compound or condition in communication with a gas contacting that compound or condition. Targeted compounds can be explosives, drugs, or poisons. The diagnostic variables can be the targeted compound can be decomposition products and other volatiles associated with the target compounds. Additionally, the diagnostic volatiles can be explosive taggant, a mixture comprising a plurality of chemicals comprising an odor signature determined from detector dog trials, or at least one volatile organic compound indicative of a disease or other medical condition. The sampling device is a capillary microextractor of volatiles (CMV). The CMV has a housing containing an absorbent for the diagnostic volatiles and includes at least two orifices in the housing that permit contacting of a gas suspected of containing the diagnostic volatiles with the absorbent. The absorbent can be a polydimethylsiloxane (PDMS) gel and can be a film on a partitioned support, such as glass fibers. The CMV is of sufficiently small size to be placed in a thermal desorption unit (TDU) or other unit included in or attached to a sample introduction port of an analytical instrument, such as an IMS or a GC-MS,

DETAILED DISCLOSURE

Figure 1:
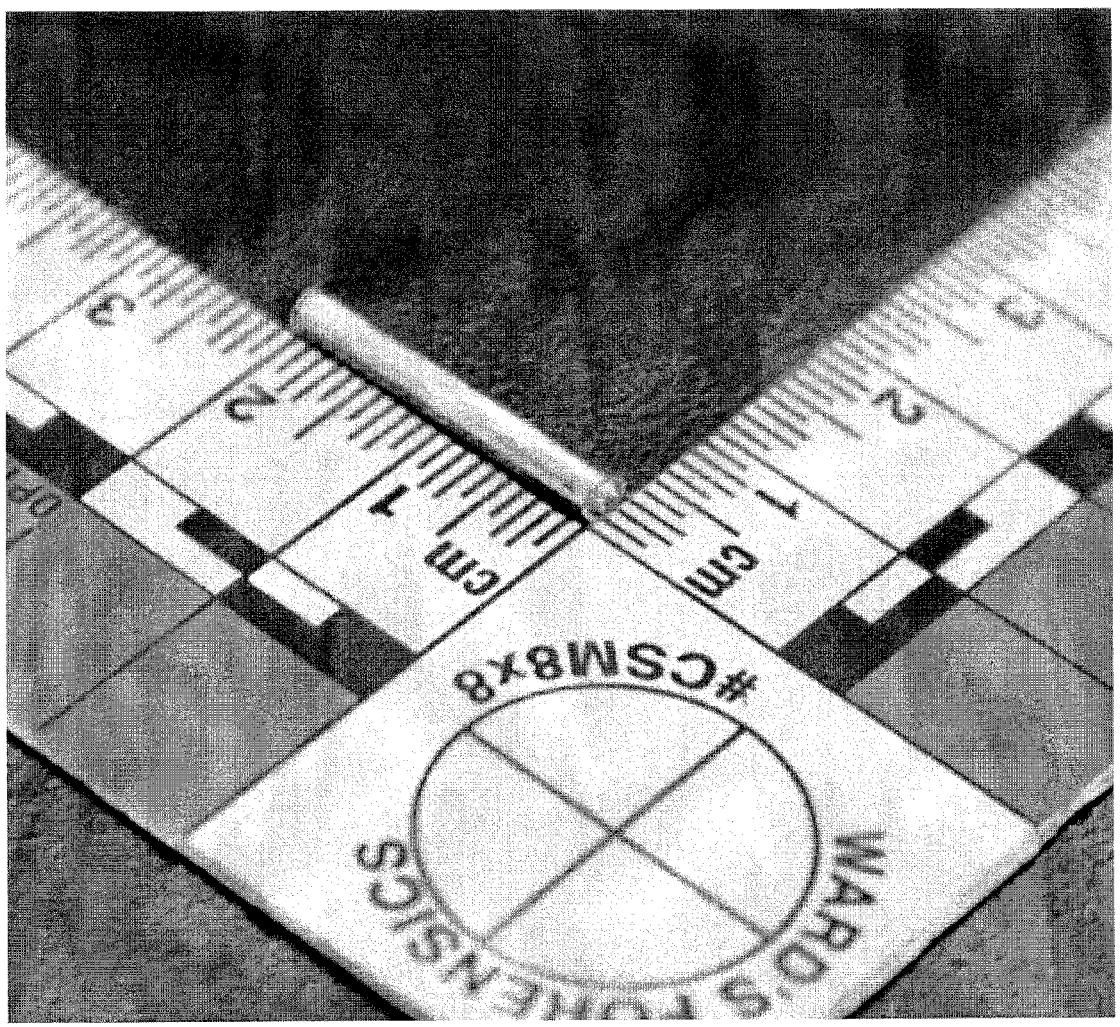
FIG. 1 shows a photograph of a capillary microextractor of volatiles (CMV) according to an embodiment of the invention illustrating the CMV's external dimensions of 20×3 mm for use with a commercial thermal desorption unit (TDU).

Embodiments of the invention are directed to a device for sampling a gas by extraction of one or more volatile organic compounds in the gas, generally, but not necessarily, air. The capillary microextractor of volatiles device, a CMV, comprises a tube or other housing that contains an absorbent, with a high surface area and/or high diffusivity. Because of the high surface area and/or inherent ability of the absorbent to permit rapid diffusion onto and/or into the absorbent, one or more chemicals contained in a gas contacting the absorbent can be rapidly sampled. The CMV can be contacted with a still gas, where simple diffusion of the gas into the tube occurs. Alternatively, gas contacting with the absorbent can be promoted by a forced flow of the gas through the housing. Flow can be forced by use of a pump, syringe, or other devices that impose a positive pressure of gas through the tube. The CMV can be used to sample the breath of a human or animal where the individual exhales directly, or with aid of an attached mouthpiece, through the CMV. A negative pressure induced flow can be forced by generation of a partial vacuum on an end of the CMV where the gas is drawn through the tube. Although the size of the tube can vary, the tube is of sufficiently small dimensions that permit it to be inserted into a sample injection system of a gas chromatography coupled to a mass spectrometer (GC-MS), ion mobility spectrometry (IMS), or even a liquid chromatograph coupled to a mass spectrometer (LC-MS), where the injection system has a thermal desorption unit where the absorbent releases the compounds at an elevated temperature. Although the CMV can be reused, the device can be inexpensive to manufacture allowing it to be discarded after a single use.

The housing of the CMV is a tube or other conduit that is a thermally stable material to a temperature of about 300° C. or more. The material is generally, but not necessarily, a non-absorbing material. For example, in embodiments of the invention, the tube can be glass, ceramic, metal, or thermally stable polymer, for example, polyimides, such a Kapton, or polybenzimidazoles. The housing is open at opposing ends to permit flow through the absorbent housed therein or can have another means that permits flow through the housing, for example, an open tube inserted into a larger closed tube where a gas pressure can be imposed in the inserted tube. The high surface area absorbent can be a thin film on a support or can have the form of an open cell foam that allows gas diffusion through the foam. The high surface area absorbent is retained in the housing by friction or by adhesion to the housing. The high surface area absorbent comprises a non-flowing material or is sufficiently viscous to be essentially non-flowing. The absorbent is amorphous and is thermally stable to temperatures in excess of about 200° C. or more, for example, stable at 250° C. or more. The absorbent or the film of the absorbent can have a glass transition temperature below normal room temperature; generally, but not necessarily, the material has a glass transition temperature ($T_g$) that is below the lowest temperatures encountered under the conditions where sampling would occur, for example, a $T_g$ of about −10° C., −20° C., −30° C., or lower in temperature. In embodiments of the invention, the absorbent includes a rigid support material that is stable to at least the temperature of the amorphous film.

For example, in embodiments of the invention, the absorbent can be a polydimethylsiloxane (PDMS) gel. The PDMS gel can be a crosslinked homopolymer or can be a copolymer with other functional groups, for example, $C_1$ to $C_4$ alkoxy groups, $C_2$-$C_{18}$ alkyl groups, phenyl groups, hydrogens, vinyl groups, aminopropyl groups, any other functional groups, or any combination of functional groups. The other functional groups can be functionalized siloxane repeating units. The other functional groups can be those formed upon reaction of a PDMS homopolymer or PDMS copolymer with divinyl benzene or other olefin comprising compounds that can provide the other functional groups upon reaction, for example, reaction during curing the PDMS gel. The support is a highly partitioned material that can be packed and readily retained within the housing of the CMV. For example, the support can be glass, ceramic or metal fibers, or can be interlinking helices or other particulate structures of shapes and sufficiently sized to avoid easy removal from the housing when a flow is induced through the CMV or when vibration and/or shock is experienced by the CMV during use or transport. For transport, the orifices of the CMV can be capped with a cap that inhibits exchange of air. Caps can be made of a metal, for example, aluminum, or of a non-absorbing plastic, or the cap can be lined with a metal liner, glass liner, or other liner that is non-absorbing.

The CMV allows sampling in the field, at a medical facility, or in a home, where an analytical unit, such as a GC-MS or IMS is not readily available. The CMV can have its orifices capped or sealed for transport to a laboratory for testing for the presence of diagnostic volatiles. For example, the diagnostic volatiles can be explosives, explosive taggants, drugs, poisons, their decomposition products, or a mixture that comprises a chemical odor signature known from detector dog trials, where a head-space is sampled by the CMV. For example, in an embodiment of the invention, the CMV can be inserted into a small opening of a suspicious or routine container and a vacuum created on the exterior end of the CMV to draw the gas of the head space through the absorbent at a rate and for a duration that has been assessed to be sufficient to collect sufficient analytical quantities of the suspected diagnostic volatile in the suspicious container. CMVs can be labeled, for example, on the housing, such that they can be distributed over an area and subsequently identified where they were placed for absorbing diagnostic volatiles. CMVs can be labeled to indicate what diagnostic variable is preferably absorbed by the CMV such that an optimal CMV for a specific sampling is readily identified before use.

In other embodiments of the invention, the CMV can be used for traffic and civil law enforcement. For example, sampling is carried out for the detection of ingested illegal drugs by an individual stopped because of suspicion of intoxication, where sampling can be carried out by requiring the individual to exhale directly, or with aid of an attached mouthpiece, through the CMV. The CMV can include a visible moisture detector to assure that the individual has exhaled to provide the desired sample. In another embodiment of the invention, the CMV is used for medical diagnostic purposes, where the patient exhales through a CMV and the CMV is analyzed for one or more volatile organic compounds indicative of a disease or other adverse medical condition.

The CMV can sample a head-space or other gas volume that is as little as about three liters where the quantity of a diagnostic volatile in the gas volume can be as little as a nanogram or less. The sampling process can be completed in as little as a few second, for example, 20 seconds or less to more than a minute. For example, sample collection can be for 5 to 10 minutes in duration. The CMV concentrates the compounds in the headspace onto and/or into the absorbent. In this manner, a suspected compound in the head space that is at a vapor concentration of only a few parts per trillion in a head space as small as about three liters can be collected with a sufficient sample size for analysis when desorbed from the CMV during analysis.

In an embodiment of the invention, the CMV is sized to be placed into a thermal desorption device that delivers a sample into a GC, such as a GC interfaced with a mass spectrometer (GC-MS). In an exemplary embodiment of the invention, the CMV consists of a 20 mm-long glass tube having an external diameter of 3 mm and an internal diameter of 2.1 mm that is packed with about 10 mg of polydimethylsiloxane gel coated silica fibers. These dimensions allow the CMV to be inserted into a liner of a thermal desorption unit (TDU), such as a Thermal Separation Probe available from Agilent Technologies, that can be placed directly into an injection system of a GC-MS.

In an embodiment of the invention, the CMV is placed in the metastable He gas stream of a Direct Analysis in Real Time (DART®) that enters the inlet of a mass spectrometer. In this manner, the excited state He atom collides with an atmospheric pressure water molecule, which forms a protonated water cluster that can protonate the compound in the CMV, which is then entrained into the inlet of the mass spectrometer. DART® systems are commercially available from Joel Ltd.

Figure 2:
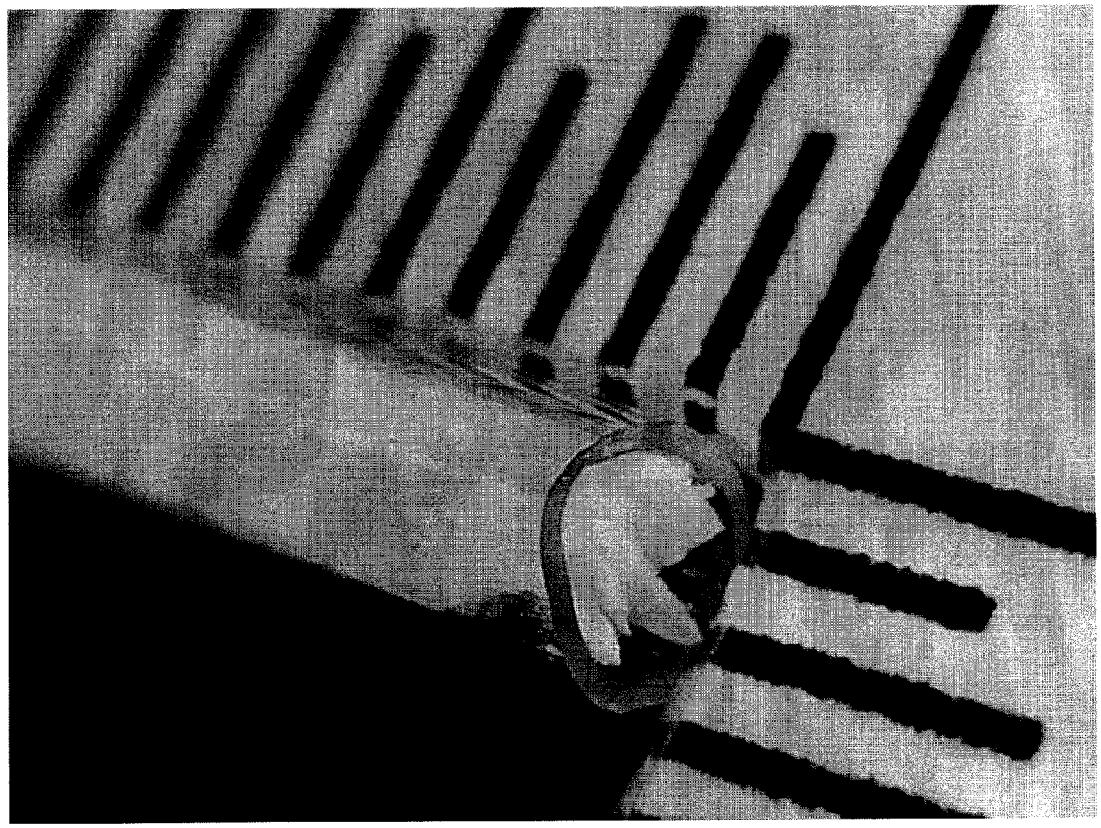
FIG. 2 shows a magnification of the photograph of an end of the CMV of FIG. 1, where the packing of the absorbent of a sol-gel PDMS on glass fiber strips is loaded in the interior of the 2.1 mm ID glass tube, according to an embodiment of the invention.
Figure 3:
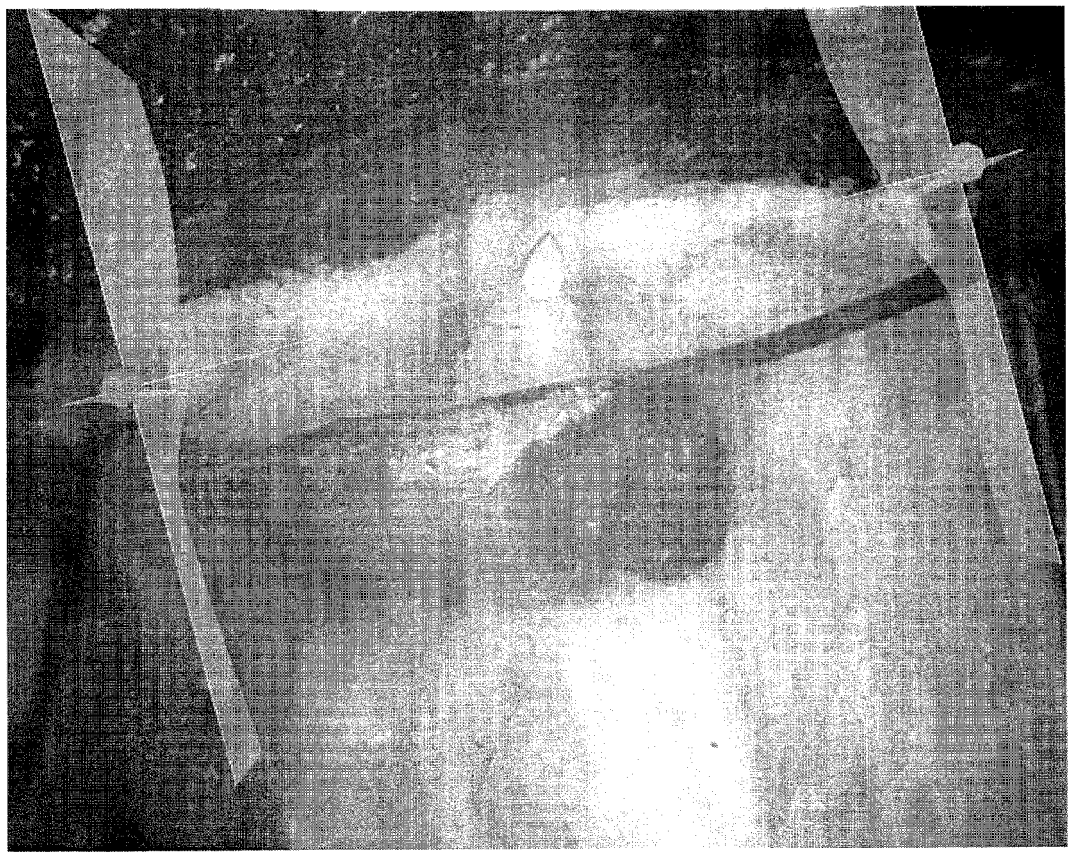
FIG. 3 shows a highly magnified photograph of the end of a CMV, as shown in FIGS. 1 and 2, according to an embodiment of the invention.
Figure 4:
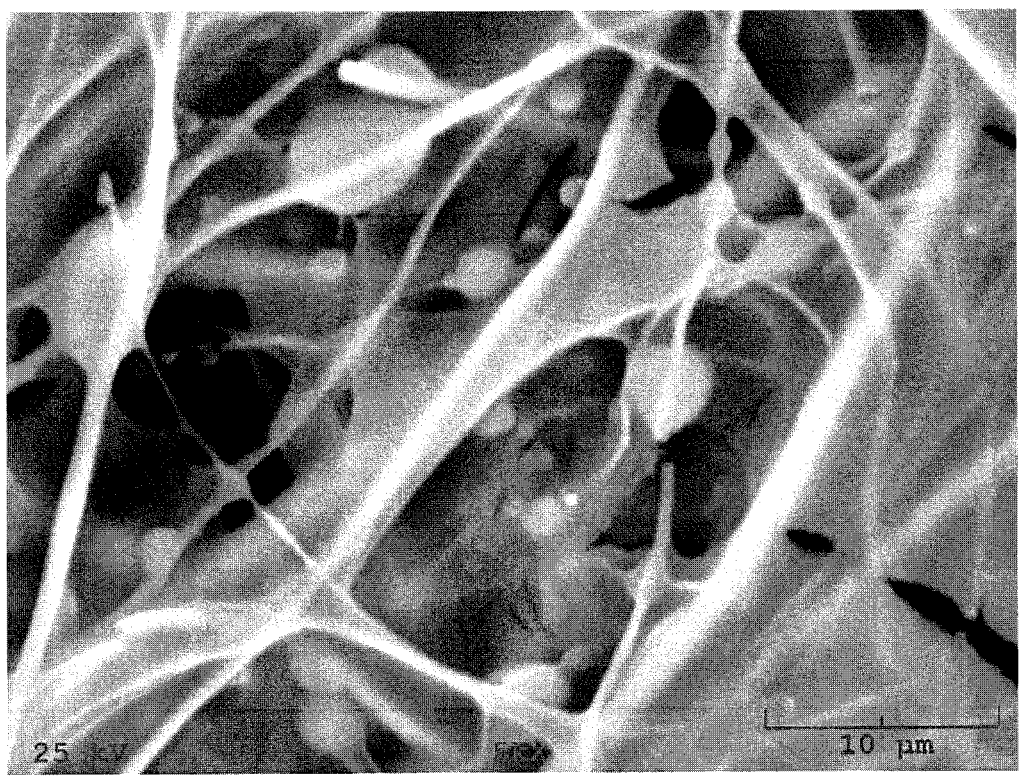
FIG. 4 is a scanning electron microscopy image of an absorbent of a sol-gel PDMS coating on glass fibers for a CMV, according to an embodiment of the invention.

In an exemplary embodiment, glass fiber filter circles (G6, Fisherbrand, Pittsburgh, Pa.) were coated using a sol-gel polydimethylsiloxane (PDMS) solution. The sol-gel PDMS solution was prepared by dissolving 6.40 g vinyl-terminated PDMS (Gelest, Morrisville, Pa.) in 8 mL of dichloromethane (DCM) followed by addition of 3.42 mL of methyltrimethoxysilane (MTMOS) (Fluka, Steinheim, Germany) and 1.67 g of polymethylhdrogensiloxane (PMHS) (Sigma-Aldrich), and subsequently 2.73 mL of TFA (Acros) (5% water v/v). The solution was mixed using a vortex stirrer and allowed to stand for 30 minutes before coating. The glass fiber circles were dipped into the sol-gel PDMS solution or spin-coated with the sol-gel PDMS solution and subsequently placed in a desiccator for 12 hours. The PDMS coated glass fiber circles were placed under DCM for 10 minutes and placed in an oven at 40° C. for 12 hours. The PDMS coated glass fiber circles were cured in an oven under a nitrogen atmosphere at 120° C. for 1 hour, 240° C. for 1 hour, and 300° C. for 3 hours. Coated circles were cut into strips of about 1 to 2 mm. The sol-gel PDMS coated glass-fiber strips were packed into 2.1 mm ID, 3 mm OD×20 mm long glass tubes, as can be seen in FIGS. 1-3. The exemplary sol-gel comprising absorbent of the CMV, according to embodiments of the invention, has a surface area in excess of 2 m²/g, which is 15,000 times that of state of the art SPMEs. As can be seen in FIG. 4, the sol-gel PDMS coating is conformed to the individual fiber to a large extent, allowing for a porous structure of the gel covered fibers. In addition to the absorbent comprising a sol-gel PDMS on glass fibers, other suitable absorbent materials are disclosed in: Almirall et al. U.S. Patent Application Publication No. 2009/0084201; Almirall et al. U.S. Patent Application Publication No. 2009\0309016; Guerra et al., *J. Sep. Sci.* 2008, 31, 2891-8; and Guerra-Diaz et al., *Anal. Chem.* 2010, 82, 2826-35, which are incorporated herein in their entirety.

All patent applications and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A capillary microextractor of volatiles (CMV), comprising:
   a housing having at least two orifices; and
   an absorbent comprising a film on a support, wherein the support comprises a plurality of thermally stable fibers and the film is an amorphous material with a thermal stability of at least 200° C., where the absorbent is porous and/or partitioned, and wherein a gas can diffuse through the housing orifices and contact the absorbent.

2. The CMV of claim 1, wherein the housing comprising a material that is thermally stable to at least 300° C.

3. The CMV of claim 1, wherein the housing is a glass tube.

4. The CMV of claim 1, wherein the amorphous material has a glass transition temperature below −10° C.

5. The CMV of claim 1, wherein the absorbent comprises a film of a polydimethylsiloxane gel (PDMS gel) on a plurality of glass fibers.

6. The CMV of claim 5, wherein the PDMS gel comprises dimethylsiloxane repeating units, and, optionally, one or more functionality selected from hydrogen, $C_1$ to $C_4$ alkoxy groups, $C_2$-$C_{18}$ alkyl groups, phenyl groups, vinyl groups, aminopropyl groups, or any combination thereof.

7. A method of sampling for one or more diagnostic volatiles, comprising:
   providing a CMV according to claim 1,
   contacting the CMV with a gas suspected of comprising at least one diagnostic volatile, wherein the diagnostic volatile is absorbed by the CMV; and
   optionally, sealing the CMV with a cap for transportation or storage.

8. The method of claim 7, wherein the diagnostic volatile is: an explosive; an explosive taggant; a drug; a poison; a decomposition product of an explosive, drug, or poison; a mixture comprising a plurality of chemicals comprising an odor signature determined from detector dog trials; or at least one volatile organic compound indicative of a disease or other medical condition.

9. The method of claim 7, wherein contacting comprises diffusion of the diagnostic volatiles into the CMV upon placement of the CMV in contact with a volume of gas suspected of containing one or more of the diagnostic volatiles.

10. The method of claim 7, wherein contacting comprises forcing flow of a volume of gas suspected of containing one or more of the diagnostic volatiles through the orifices of the CMV and through the absorbent of the CMV.

11. A method for analyzing for one or more diagnostic volatiles, comprising:
    providing a CMV according to claim 1 having at least one diagnostic volatile absorbed therein;
    placing the CMV into a thermal desorption unit (TDU);
    coupling the TDU to an inlet port of an instrument for analysis of a volatile; and
    heating said TDU to a temperature sufficient for desorbing the diagnostic volatile from the CMV, wherein the diagnostic volatile is introduced into the instrument for analysis of a volatile.

12. The method of claim 11, wherein the instrument for analysis of a volatile comprises a gas chromatograph (GC), an ion mobility spectrometer (IMS), a liquid chromatograph (LC), or a mass spectrometer (MS).

13. A method for analyzing for one or more diagnostic volatiles, comprising:
    providing a CMV according to claim 1 having at least one diagnostic volatile absorbed therein;
    inserting the CMV into ionized He gas stream coupled to an inlet port of a mass spectrometer (MS).

* * * * *